United States Patent [19]

Bajaj

[11] Patent Number: 5,846,710
[45] Date of Patent: Dec. 8, 1998

[54] METHOD FOR THE DETECTION OF GENETIC DISEASES AND GENE SEQUENCE VARIATIONS BY SINGLE NUCLEOTIDE PRIMER EXTENSION

[75] Inventor: S. Paul Bajaj, St. Louis, Mo.

[73] Assignee: St. Louis University, St. Louis, Mo.

[21] Appl. No.: 103,408

[22] Filed: Aug. 6, 1993

Related U.S. Application Data

[63] Continuation of Ser. No. 608,225, Nov. 2, 1990, abandoned.

[51] Int. Cl.$^6$ .............................. C12Q 1/68; C12P 19/34; C07H 21/04; C12N 15/00
[52] U.S. Cl. .......................... 435/6; 435/91.1; 435/91.2; 536/23.1; 536/23.5; 536/24.33; 935/76; 935/77; 935/78
[58] Field of Search ................................. 435/6, 91, 91.1, 435/91.2, 183; 536/23.1, 24.3, 24.33, 25.4; 935/6, 17, 19, 78, 80, 76, 77

[56] References Cited

U.S. PATENT DOCUMENTS

| | | | |
|---|---|---|---|
| 4,656,127 | 4/1987 | Mundy | 435/6 |
| 4,683,202 | 7/1987 | Mullis | 435/91 |
| 4,851,331 | 7/1989 | Vary et al. | 435/6 |
| 4,883,750 | 11/1989 | Whiteley et al. | 435/6 |

FOREIGN PATENT DOCUMENTS 0246864  11/1987  European Pat. Off. .

OTHER PUBLICATIONS

Newton et al. Nucl. Acids. Res. 17(7):2503 (1989).
Kuppuswamy et al., "A New Use of Polymerase Chain Reaction (PCR) in Carrier Detection of Hemophilia–B Due to Point Mutations", American Soc. of Hematology, Abstract, 1989.
Spitzer et al., "Molecular Defect in Factor IX", Journal of Biological Chemistry, vol. 263, No. 22, pp. 10545–10548, Aug. 5, 1988.
Ware et al., "Genetic Defect Responsible for the Dysfunctional Protein:Factor IX", Blood, vol. 72, No. 2, pp. 820–822, Aug., 1988.
Bajaj et al., "Experimental and Theoretical Evidence Supporting the Role of Gly–363 in Blood Coagulation Factor IXa", pp. 1–20.
Spitzer et al., "Replacement of isoleucine–397 by threonine in the clotting proteinase Factor IXa", Biochem. J., 265, 7 pages, (1990).
Rossiter et al., "Molecular Scanning Methods of Mutation Detection", Jour. of Biol. Chem., vol. 265, No. 22, pp. 12753–12756, Aug. 5, 1990.
Landegren et al., "DNA Diagnostics–Molecular Techniques and Automation", Science, vol. 242, pp. 229–237, Oct. 14, 1988.
Caskey, "Disease Diagnosis by Recombinant DNA Methods", Science, vol. 236, pp. 1223–1230, Jun. 5, 1987.
Nassal et al. Nucleic Acid Res 18(10):3077 (1990).
Ehlen et al. Biochem. + Bio Phy Res. Com. 160(2):441 (1989).
Newton et al Nucl. Acid. Res. 17(7):2503 (1989).
Wu et al. P.N.A.S. 86:2757 (1989).
Riordan et al. Science 245:1066 (1989).
Rummens et al Science 245:1059 (1989).

*Primary Examiner*—Bradley L. Sisson
*Attorney, Agent, or Firm*—Senniger, Powers, Leavitt & Roedel

[57] ABSTRACT

Method for screening a sample oligonucleotide for a variation in sequence at a predetermined position thereof relative to a nucleic acid the sequence of which is known, wherein the sample oligonucleotide is provided as a single stranded molecule, the single stranded molecule is mixed with an inducing agent, a labeled nucleotide, and a primer having a sequence identical to a region flanking the predetermined position to form a mixture, the mixture having an essential absence of nucleotides constituted of bases other than the base of which the labeled nucleotide is constituted, the mixture is subjected to conditions conducive for the annealing of the primer to the single stranded molecule and the formation of a primer extension product incorporating the labeled nucleotide, and the mixture is analyzed for the presence of primer extension product containing labeled nucleotide.

20 Claims, 4 Drawing Sheets

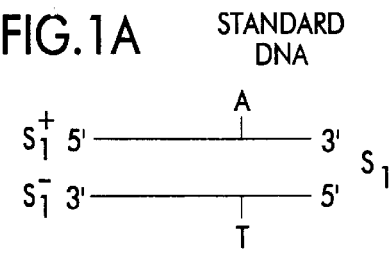
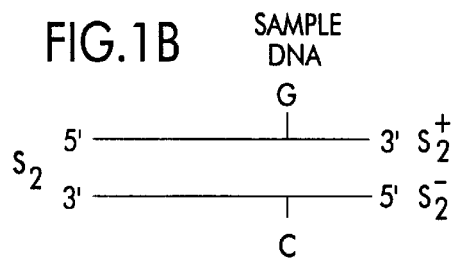
FIG. 1A  STANDARD DNA
FIG. 1B  SAMPLE DNA
STEP 1  DENATURE DNA
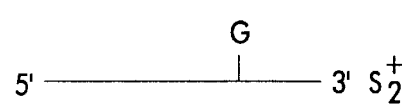
STEP 2  ADD PRIMER AND ANNEAL
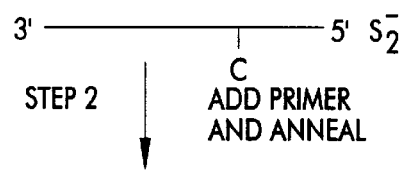
STEP 3  DIVIDE INTO SEPARATE REACTION MIXTURES AND ADD LABELED NUCLEOTIDE AND INDUCING AGENT
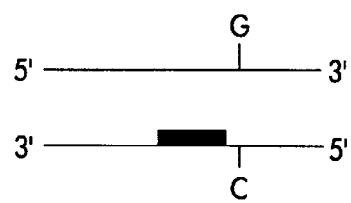
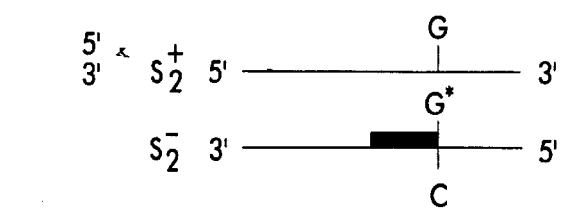
STEP 4  ANALYZE PRIMER EXTENSION PRODUCT FOR LABELED NUCLEOTIDE
PRIMER NOT LABELED
PRIMER LABELED FIG. 2A
Family 1
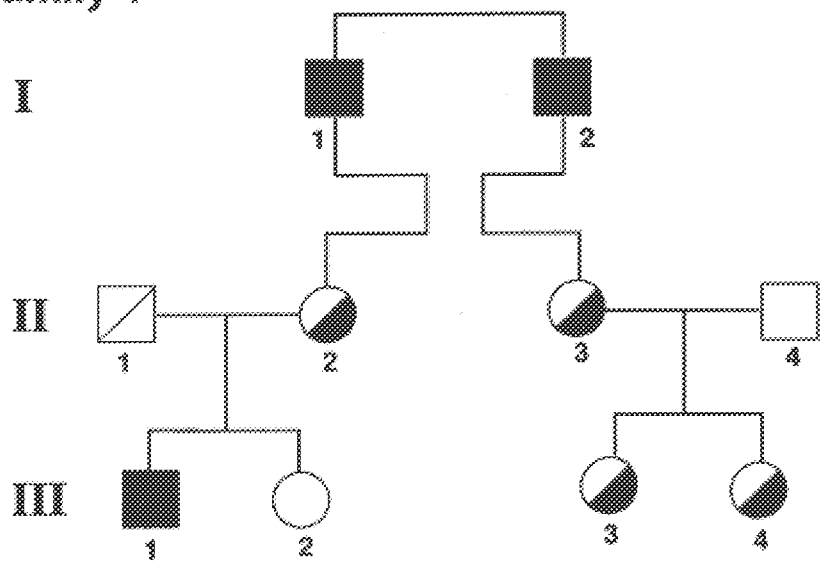
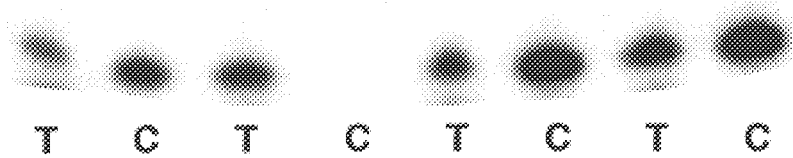
5'- GCAATGAAAGGCAAATATGGAATA — normal   SEQ ID 1
5'- ——————————————— C — mutant   SEQ ID 2

FIG. 2B
Family 2
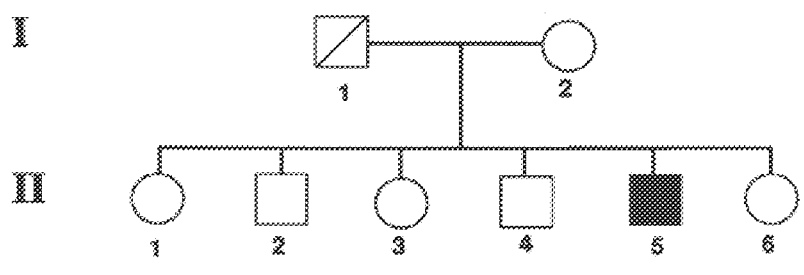

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:

( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCAATGAAAG GCAAATATGG AATA 24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCAATGAAAG GCAAATATGG AACA 24

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AAGGAGGTAG AGATTCATGT CAAGGA 26

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AAGGAGGTAG AGATTCATGT CAAGTA 26

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CTGGCACCAT TAAAGAAAAT ATCATCTTT 29

( 2 ) INFORMATION FOR SEQ ID NO:6:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:6:

CTGGCACCAT TAAAGAAAAT ATCATT                                                                                  2 6

METHOD FOR THE DETECTION OF GENETIC DISEASES AND GENE SEQUENCE VARIATIONS BY SINGLE NUCLEOTIDE PRIMER EXTENSION

This is a continuation of application Ser. No. 07/608,255 filed on Nov. 2, 1990, now abandoned.

BACKGROUND OF THE INVENTION

The present invention relates, in general, to a method for determining the sequence of a sample DNA fragment at a predetermined position, and in particular, to a method for the detection of known genetic abnormalities or gene sequence variations resulting from nucleotide substitutions, translocations, insertions or deletions of as little as one nucleotide.

One goal of clinical molecular biology is to identify the mutations that cause genetic diseases and to develop strategies and related technologies to diagnose them. Towards this end, in the last decade or so many methodological advances have been made to detect human genetic abnormalities at the DNA level. These include indirect methods such as linkage analysis using the Southern blotting technique where the inheritance of a disorder is associated with the presence of a restriction fragment-length polymorphism (RFLP), e.g., Duchenne muscular dystrophy. Other indirect methods include ribonuclease A cleavage at mismatches in probe RNA:sample DNA duplexes or denaturing gradient gel electrophoresis for mismatches in probe DNA:sample DNA duplexes, e.g., β-thalassemia. The direct methods include detection with the restriction enzymes or with the allele specific oligonucleotide (ASO) probes, e.g., the sickle cell mutation. See, for example Landegren et al., *Science* 242:229–237, 1988; Rossiter et al, *J. Biol. Chem.* 265:12753–12756, 1990.

A majority of the above approaches have now been combined with the polymerase chain reaction (PCR) for diagnosis of the sequence variations. Initially, the target DNA is amplified by PCR followed by the analysis of the sequence variation by ASO hybridization, e.g., the sickle cell mutation, restriction enzyme analysis, e.g., the sickle cell mutation and some hemophilia B mutations, ribonuclease A cleavage, e.g., α1-antitrypsin gene Z mutation, denaturing gradient gel electrophoresis, e.g., hemophilia A mutations, chemical cleavage, e.g., hemophilia B mutations, and the ligation of oligonucleotide pairs or the ligation amplification, e.g., the sickle cell mutation. Recently, an allele specific PCR (ASPCR) amplification technique to diagnose point mutations has also been introduced, Wu et al., *Proc. Natl. Acad. Sci.* 86:2757–2760, 1989.

Some of the above techniques do not detect all mutations that involve single nucleotides and are technically quite demanding. Others require optimization of conditions that allows specific hybridization of the ASO probe or specific amplification of the selected allele by ASPCR.

SUMMARY OF THE INVENTION

Among the objects of the invention, therefore, may be noted the provision of a method for the detection of abnormal alleles in those genetic diseases where the frequency of occurrence of the same mutation is high, and in other genetic diseases where multiple mutations cause the disease and the sequence variation in an affected member of a given family is known; the provision of a method for determining the sequence of a genomic DNA sample at a predetermined position thereof; the provision of such a method in which nucleotide sequence variations of as little as one nucleotide can be detected; and the provision of such a method which is relatively rapid and not technically demanding.

Briefly, therefore, the present invention is directed to a method for detecting a known genetic abnormality or gene sequence variation resulting from a nucleotide substitution, translocation, insertion or deletion at a predetermined position in a sample DNA fragment by single nucleotide primer extension. The method comprises providing the sample DNA fragment as a denatured molecule and mixing it with an inducing agent, a primer having a sequence complementary to a region flanking the predetermined position, and a labeled nucleotide to form a mixture. The mixture has an essential absence of nucleotides constituted of bases other than the base of which the labeled nucleotide is constituted. The mixture is subjected to conditions conducive for the annealing of primer to the single stranded molecule and the formation of a primer extension product incorporating the labeled nucleotide. The mixture is thereafter analyzed for the presence of primer extension product which has incorporated the labeled nucleotide.

Other objects will be in part apparent, and in part pointed out hereinafter.

BRIEF DESCRIPTION OF THE DRAWINGS

FIGS. 1A and 1B are schematic diagrams of a preferred embodiment of the method of the present invention.

FIG. 2 is a diagram depicting the results of Example 1.

DETAILED DESCRIPTION OF THE PREFERRED EMBODIMENTS

Figure 3:
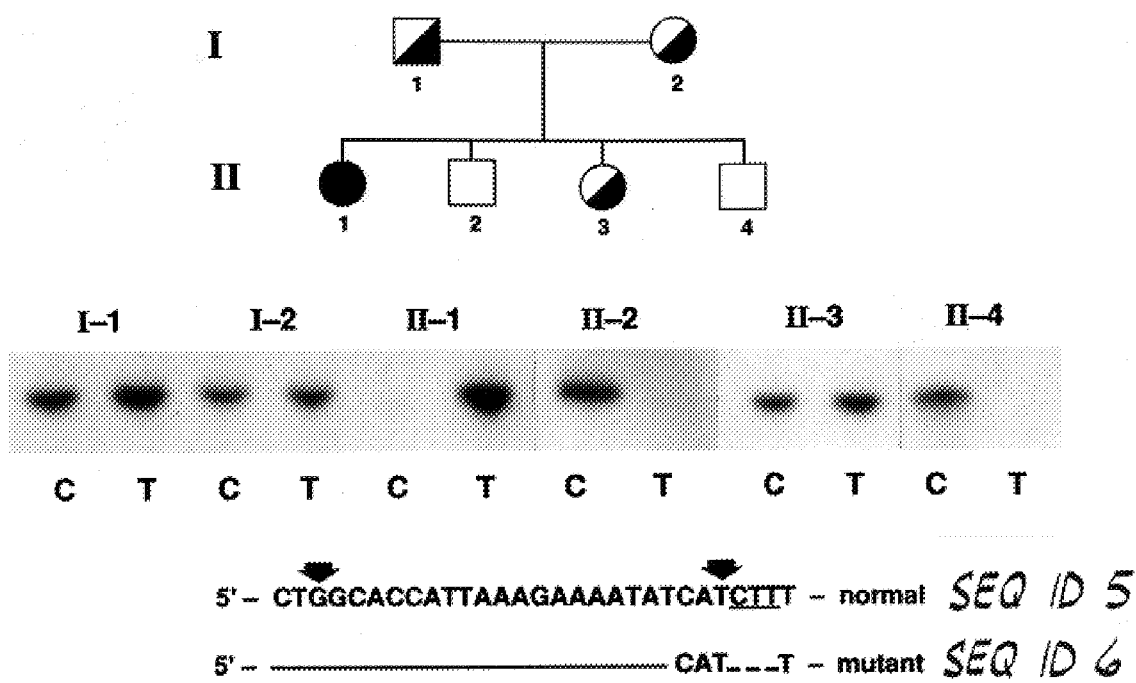
FIG. 3 is a diagram depicting the results of Example 2.

The term "DNA" or "DNA fragment" as used herein is defined as a molecule comprised of two complementary strands of approximately 30 or more deoxyribonucleotides.

The term "primer" as used herein refers to an oligonucleotide which is capable of acting as a point of initiation of synthesis when placed under conditions in which synthesis of a primer extension product which is complementary to a nucleic acid strand is induced, i.e., in the presence of nucleotides and an inducing agent such as DNA polymerase and at a suitable temperature and pH. The primer must be sufficiently long to prime the synthesis of an extension product in the presence of the inducing agent. The primer is preferably an oligodeoxyribonucleotide and typically contains about 18 nucleotides.

The term "inducing agent" as used herein is defined as any compound or system which will function to accomplish the synthesis of primer extension products, including enzymes. Suitable enzymes for this purpose include, for example, E. Coli. DNA polymerase I, Klenow fragment of E. Coli. DNA polymerase, other available DNA polymerases, and other enzymes, including heat-stable enzymes which will facilitate addition of the labeled nucleotide in the proper manner to form the primer extension product.

In accordance with the present invention, it has been found that the nucleotide sequence of a genomic DNA sample can be analyzed for sequence variations and that variations of as little as one nucleotide can be detected relatively rapidly according to a method which is not technically demanding. This method may be conveniently used to detect the presence of abnormal alleles in those genetic diseases where frequency of occurrence of the same mutation is high (e.g., cystic fibrosis and sickle cell disease), and in others where multiple mutations cause the disease and the sequence variation in an affected member of a given family is known (e.g., hemophilia B).

A preferred embodiment of the method of the present invention is depicted schematically in FIG. 1 in the context of a hypothetical wild-type, "standard" DNA fragment $S_1$ and a hypothetical sample DNA fragment $S_2$. For purposes of this illustration, the standard and sample DNA fragments $S_1$ and $S_2$ are assumed to be identical except that the sample fragment $S_2$ has a nucleotide substitution at a predetermined position B relative to the standard fragment; the standard fragment has base pairs A and T (strands $S_1^+$ and $S_1^-$, respectively) whereas the sample fragment has base pairs G and C (strands $S_2^+$ and $S_2^-$, respectively) at the predetermined position.

To confirm that (or determine whether) sample DNA fragment $S_2$ has a sequence variation at the predetermined position B relative to the standard, the sample DNA fragment $S_2$ is denatured into single stranded molecules $S_2^+$ and $S_2^-$ (step 1). Primer P which is complementary to single stranded molecule $S_2^-$ at a position immediately flanking the 3' end of the predetermined position B is then annealed to the single stranded molecule $S_2^-$ (step 2). The resulting product is then divided into separate aliquots, and an inducing agent and a labeled nucleotide are added to each aliquot to form separate reaction mixtures (step 3). The labeled nuclueotide added to one of the reaction mixtures is labeled adenine whereas the labeled nucleotide added to other reaction mixture is labeled guanine. Each reaction mixture is allowed to undergo single nucleotide primer extension with the labeled nucleotide, i.e., extension with nucleotide constituted of only one of the four types of bases (adenine in one of the reaction mixtures in this illustration and guanine in the other) and thereafter analyzed for the presence of primer extension product incorporating labeled nucleotide (step 4). In this illustration, the incorporation of labeled guanine and the lack of incorporated labeled adenine positively identifies the sequence of the sample DNA fragment $S_2$ at the predetermined position B as being a variant of the standard DNA.

It should be noted that the primer P in FIG. 1 may have alternatively comprised a nucleotide sequence which is complementary to single stranded molecule $S_2^+$ at a position immediately flanking the 3' end of the predetermined position B. If such a primer were selected, labeled cytosine would be substituted for labeled guanine in step 3.

Unlike standard PCR, the object of single nucleotide primer extension is not amplification of oligodeoxyribonucleotides. Rather, the object is to identify the nucleotide at a predetermined point of potential variation or mutation in a sample gene, the sequence of which is otherwise known. Thus, it is preferred that only one primer be included in the reaction mixture. Similarly, it is also preferred that the reaction mixture comprise nucleotide constituted of only one type of base. Inclusion of a plurality of primers and/or nucleotides would tend to eliminate the specificity of the reactions.

The rapidity and ease with which a sample DNA fragment is analyzed at a predetermined position relative to a known, standard DNA sequence is thus achieved by the composition of the reaction mixture and by the fact that only one cycle of chain extension is necessary. Because the reaction mixture contains nucleotide constituted of only one type of base and a primer having a sequence complementary to only one of the strands of the sample DNA fragment, the incorporation of labeled nucleotide into a primer extension product directly and positively confirms the sequence of the sample DNA at the predetermined position. In addition, by using separate reaction mixtures each containing a different labeled nucleotide, the extent of variation in the sample DNA at the predetermined position is positively identified.

Preferably, the reaction mixture comprises about 50 to 100 ng (depending upon the length of the fragment) of the DNA sample fragment containing the putative variation site. Conveniently, the DNA sample fragment may be provided as a PCR product of copy DNA obtained from RNA or of genomic DNA. Irrespective of source, the sample DNA is provided as single stranded molecules (preferably by denaturation where genomic DNA is the source). The reaction mixture is then subjected to conditions suitable for the annealing of the primer to the single stranded molecules and the formation of primer extension product incorporating the labeled nucleotide. Upon completion of that cycle, the primer extension product is separated from free labeled nucleotide preferably by denaturing polyacrylamide gel electrophoresis. The oligomers are then analyzed for the presence of label.

If it is desired to analyze a sample DNA fragment for purposes of determining whether the sample DNA fragment donor carries a mutant gene, two reaction mixtures can be prepared. Each contains the sample DNA fragment, a primer whose sequence is complementary to the sequence of the gene immediately flanking the 3' end of the putative mutation site and an inducing agent. One of the reaction mixtures contains a labeled nucleotide corresponding to the normal coding sequence at the putative mutation site and the other contains a labeled nucleotide corresponding to a mutant sequence. Each reaction mixture has an essential absence of nucleotides other than labeled nucleotide. Primer extension is carried out in each reaction mixture and the products are analyzed for the presence of a primer extension product containing labeled nucleotide. According to the Watson-Crick base pair rule, in the wild type only the normal base, in an affected member only the mutant base, and in carriers both the normal and the mutant base will be incorporated into the primer.

For use in the reaction mixture, nucleotides may be labeled by any appropriate means. Preferably, the nucleotides are radioactively labeled by means of incorporation of $^3H$, $^{32}S$ or $^{32}P$ and are detected by means of autoradiography. However, other methods for labeling nucleotides presently known or hereafter developed may be used in accordance with the present invention.

Similarly, upon completion of one cycle of chain extension the primer may be separated from labeled nucleotide for detection of signal by any means standard in the art. Preferably and conveniently, the reaction mixture components may be separated by denaturing polyacrylamide gel electrophoresis. When the nucleotides are radioactively labeled, this technique can be combined with audioradiography to provide rapid and convenient detection of primer extension product incorporating labeled nucleotide.

The method of the present invention is rapid and has utility in carrier detection and prenatal diagnosis of genetic diseases with a known sequence variation. For instance, Cystic Fibrosis (CF) is the most common severe autosomal recessive disorder in the Caucasian population; its clinical, physiologic and genetic aspects have been discussed recently, and a three-base pair deletion which removes $Phe^{508}$ from the putative CF protein of 1480 amino acids has been identified as the mutation which causes CF in a majority (60%) of the chromosomes Lemna et al., N. Engl. J. Med 322:291–296, 1990. The single nucleotide primer extension method of the present invention provides a rapid and convenient technique for determining an individual's status as a carrier of this mutation. If the index patient is fully informative, i.e., has haplotype 2/2 (see Example 2), single nucleotide primer extension alone can be used for carrier detection and prenatal diagnosis. If the index patient is partly informative, i.e., has haplotype 1/2, single nucleotide primer extension can still be of value in diagnosing some of the carriers (normal phenotype but one chromosome having haplotype 2) in the same family and all of the carriers in either the maternal or the paternal side of the family. Although the remainder of the CF mutations cannot presently be detected using single nucleotide primer extension because the causative mutations are unknown, upon identification of these mutations single nucleotide primer extension will be useful on a more general basis for the CF gene screening.

Similarly, hemophilia B is an X-linked bleeding disorder caused by the absence of factor IX coagulant activity. Among others, hemophilia B point mutations in the protease domain (exon VIII) of factor IX have recently been described which lead to impaired macromolecular catalysis by the mutated enzymes (Bajaj et al., *J. Biol. Chem.* 265:2956–2961, 1990; Spitzer et al., *Biochem. J.* 265:219–245, 1990). Knowing the causative base change in each of these families, the single nucleotide primer extension method of the present invention serves as a powerful screening tool to determine whether an individual bears this particular mutation. If so, prenatal diagnosis and determination of the carrier status of females members in such pedigrees could be accurately carried out.

In addition to detection of point mutations in hemophilia B and a deletion in the CF gene, the single nucleotide primer extension technique should also be applicable to the detection of other genetic diseases of known sequence variations, particularly the sickle cell mutation (A→T) and the α1-antitrypsin gene Z mutation (G→A). Recently, PCR in combination with ASO hybridization has been employed for determination of the HLA-DR, DQ, and DP alleles Angelini et al., *Human Immunol.* 23:77, 1988; Scharf et al., *Human Immunol.* 23:143, 1988. Similarly, the human platelet alloantigens $Pl^{A1}$ and $Pl^{A2}$ have been shown to differ only by one nucleotide (C→T) Newman et al., *J. Clin. Invest.* 83:1778–1781, 1989. Therefore, it should be possible to use single nucleotide primer extension for the direct analysis of the HLA types as well as the human platelet alloantigen (C→T) polymorphism. Moreover, single nucleotide primer extension may also find application in the early detection of Codon 12 and Codon 61 mutations in ras oncogenes which are estimated to cause as much as 30% of human tumors Kumar et al., *Science* 248:1101–1104, 1990.

Single nucleotide primer extension can also be useful in many research settings. For example, in an autosomal genetic disorder, if an investigator finds a mutation (or sequence variation) in a PCR amplified segment of the DNA (obtained from the patient) cloned into PUC 18 or M13 vector, he (or she) can readily check, using single nucleotide primer extension, whether both chromosomes carry the same mutation and, thus, distinguish between the homozygous and the compound heterozygous mutations. The mutations can also be verified in the PCR amplified fragments relatively easily by the use of the method of the present invention, thus eliminating the need for sequencing the fragments in their entirety.

The following examples illustrate the invention.

EXAMPLE 1

The method of the present invention was used to identify members from two separate families as being afflicted with or carriers of hemophilia B.

Experimental Procedures

Materials. Taq polymerase was obtained from Cetus Corporation. [α-$^{32}$P]-labeled nucleotides (10 µCi/µL, 3000 Ci/mmol) were obtained from DuPont-New England Nuclear. Genomic DNA was isolated from the blood leukocytes by standard techniques. Use of volunteer blood donor was approved by the human subjects committee of St. Louis University and of the University of Southern California.

PCR Amplification and Isolation of the Amplified DNA. The set of primers employed for PCR amplification of exon VIII corresponded to the nucleotides 30760–30780 and 31360–31379 of factor IX gene. Target sequences in the genomic DNA were amplified by standard PCR technique. Following amplification, the DNA was electrophoresed on 1% agarose gel in Tris-acetate-EDTA buffer. The segment of the gel containing the amplified region was cut out and mixed with an equal volume of phenol, pH 8.0 and frozen at −70° C. for a minimum period of 10 minutes. The sample was thawed at 37° C. for 10 minutes and briefly centrifuged in an eppendorf tube. The DNA in the upper aqueous layer was ethanol-precipitated and stored till used.

Single Nucleotide Primer Extension ("SNuPE"). Each SNuPE reaction was carried out in a 50-µL volume containing ~100 ng of the amplified DNA fragment, 1 µM of the SNuPE primer, 2 units of Taq polymerase and 1 µL of the [α-$^{32}$P]-labeled appropriate nucleotide (10 µCi/µL, 3000 Ci/mmol). The buffer used was 10 mM Tris-HCl, pH 8.3 containing 50 mM KCl, 5 mM $MgCl_2$ and 0.001% (w/v) gelatin. The samples were subjected to one cycle consisting of 2-minutes denaturation period at 94° C., 2-minutes annealing period at 60° C., and 2-minutes primer extension period at 72° C. The sequence of the SNuPE primer for each family is given in FIG. 2. Details of gel electrophoresis and autoradiography for detection of the extended primer are also given in legends to FIG. 2.

Figure Legends

Family 1 has Ile397Thr (nucleotide 31,311 T→C) mutation Spitzer et al., *Biochem. J.* 265:219–225, 1990 and family 2 has Gly363Val (nucleotide 31,209 G→T) mutation Bajaj et al., *J. Biol. Chem.* 265:2956–2961. Affected members in both families have hemophilia B. Initially, exon VIII from each subject was amplified from the genomic DNA by the standard PCR using the two primers corresponding to nucleotides 30760–30780 and 31360–31379 of factor IX gene. The isolated amplified fragments were used for SNuPE reactions (for details see "Experimental Procedures"). The extension of the SNuPE primer for each reaction was then analyzed by gel electrophoresis and autoradiography. A 5 µl-aliquot of each sample was mixed with an equal volume of gel loading buffer (80% formamide, 50 mM Tris-borate pH 8.3, 1 mM EDTA, 0.1% xylene cyanol, 0.1% bromophenol blue), heat denatured at 90° C. for 1 min, and loaded onto a 6% polyacrylamide gel containing 8M urea. Gels (17 cm) were run at 300 V for 2 hours to obtain adequate resolution of the extended primer from the free nucleotide. Autoradiographs of gels were made by overlaying Kodak X-AR5 film and exposing for 20 to 30 minutes at room temperature. The sequence of SNuPE primer for each family is indicated by the top two arrows. The causative base change in each family is also depicted. For each individual two SNuPE reactions were carried out; the single radiolabeled nucleotide included in the SNuPE reaction was either T (normal) or C (mutant) for family 1 and was either G (normal) or T (mutant) for family 2. When only the wild-type base was incorporated into the SNuPE primer, the subject was considered normal; when only the mutant base was incorporated into the primer, the subject was considered a hemophiliac and when both bases (one in each reaction) were incorporated into the primer, the subject was considered a carrier of the disease. The autoradiographs depicted in this figure show results of limited subjects only. Symbols: square, male; circle, female; filled symbol, hemophiliac; half-filled symbol, carrier of hemophilia; slashed symbol, deceased.

RESULTS

In both families, prior to defining the mutation sites within exon VIII of the factor IX gene, attempts to establish the carrier status of the female members in these pedigrees employing IX:C/IX:Ag ratios and linked RFLPs analyses were not successful. After identification of the causative base change (T→C at position 31,311) in family 1, SNuPE was used to determine the carrier status of the females in this family; $III_2$ was identified a noncarrier and $III_3$ and $III_4$ were identified as carriers of the disease (FIG. 2). The obligatory carrier status of $II_2$ and $II_3$ was also confirmed. Since it has been estimated that approximately 1 out of 5 hemophilia B patients (with factor IX sequence changes) carries the T→C mutation at position 31,311, SNuPE could serve as a powerful screening tool to determine whether or not the index patient bears this particular mutation. If so, prenatal diagnosis and determination of the carrier status of females members in such pedigrees could be accurately carrier out using SNuPE.

In family 2 (FIG. 2), there is no prior history of bleeding. Subject $I_2$ in this family had unilateral ovariectomy before any of her children were conceived; thus, all of her offspring are the product of ova from one ovary. Again, attempts to establish the carrier status in this pedigree using IX:C/IX:Ag ratios and linked RFLP's were not successful. Once the mutation was identified, SNuPE was applied to determine the carrier status of females in this family. Results are given in FIG. 2. None of the females, including the mother of the patient, had the mutated allele. Thus, the mutation causing hemophilia B in Subject $II_5$ is a de novo mutation and in all probability occured in a single ovum that resulted in the II5 zygote.

EXAMPLE 2

Using the procedures outlined in Example 1, individuals were screened for the $Phe^{508}$ deletion mutation present in 60% of cystic fibrosis chromosomes. The exon region containing the 1611–1708 bp segment of the CF gene containing the most common $Phe^{508}$ deletion mutation was amplified using the two PCR primers (C16B and C16D) used earlier by other groups Lemna et al., *N. Engl. J. Med.* 322:291–196. Following amplification, the DNA was electrophoresed on 6% polyacrylamide gel in Tris-borate-EDTA buffer. The segment of the gel containing the amplified fragment (~100 bp) was cut out and the DNA was extracted by electroelution (40 V/12 h) using the dialysis membrane tubing (Spectra/por 2) in Tris-borate-EDTA buffer. Execution of the SNuPE reaction was carried out as detailed in Example 1. The $^{32}P$-labeled single nucleotide included in the SNuPE reaction was either C (normal) or T (mutant). In a fully informative family, when only the C base is incorporated into the primer, the subject is considered normal; when only the T base is incorporated into the primer, the subject is considered a CF patient; and when both C and T were incorporated into the primer, the subject is considered a carrier of the CF gene.

Using the single nucleotide primer extension method, 34 chromosomes of 17 unrelated individuals were analyzed and it was found that none of them had the three-base pair deletion corresponding to the amino acid $Phe^{508}$ (Table 1). 74 CF chromosomes (37 CF unrelated patients) were also analyzed and it was found that 46 of them had the putative three base-pair deletion. This finding further establishes that indeed ~60% of the CF chromosomes carry the three-base pair deletion.

Using single nucleotide primer extension several new families homozygous for this mutation were also identified. Results of one family are shown in FIG. 3. (Symbols: square, male; circle, female; filled symbol, CF patient; half-filled symbol, carrier of CF gene). Each parent has one CF and one normal chromosome and the affected child ($II_1$) has two CF chromosomes, one derived from each parent. Two children ($II_2$ and $II_4$) have inherited the normal chromosome from each parent. Another child ($II_3$) inherited one normal and one CF chromosome and is a carrier of the CF disease.

TABLE 1

Prevalence of $Phe^{508}$ Deletion Mutation in Normal and CF Chromosomes as Detected by SNuPE

|  | Total | $Phe^{508}$ Deletion | % $Phe^{508}$ Deletion |
|---|---|---|---|
| Normal Chromosomes | 34 | 0 | 0 |
| CF Chromosomes (unrelated CF patients) | 74 | 46 | 62 |
| 1/1 genotype CF patients[a] | 10 | 0 | — |
| 1/2 genotype CF patients[a] | 36 | 18 | — |
| 2/2 genotype CF patients[a] | 28 | 28 | — |

[a]Haplotype 1 is defined as that in which CF mutation is at a region other than the $Phe^{508}$ deletion and haplotype 2 is defined as that in which the CF mutation is the $Phe^{508}$ deletion.

In view of the above, it will be seen that the several objects of the invention are achieved.

As various changes could be made in the above methods without departing from the scope of the invention, it is intended that the above description shall be interpreted as illustrative and not in a limiting sense.

What is claimed:

1. A method for screening a DNA fragment of a gene for variation of nucleotide sequence at a predetermined position relative to the nucleotide sequence of the corresponding wild-type gene, the sequence of the wild-type gene being known at the predetermined position, the method comprising the steps of:
    (a) providing the DNA fragment as a single stranded molecule,
    (b) mixing the single stranded molecule with an inducing agent, an unlabeled primer having a nucleotide sequence complementary to a region flanking the predetermined position, and a labeled nucleotide to form a mixture, the mixture having an essential absence of nucleotides constituted of bases other than the base of which the labeled nucleotide is constituted,
    (c) subjecting the mixture to conditions conducive for the annealing of the primer to the single stranded molecule and the formation of a primer extension product incorporating the labeled nucleotide,
    (d) after step, analyzing the mixture for the presence or absence of primer extension product incorporating the labeled nucleotide, the analysis being carried out under conditions such that any primer which did not form a primer extension product incorporating the labeled nucleotide in step (c) is present throughout the analysis, and
    (e) determining whether the sequence of the DNA fragment at the predetermined position is the same as or a variant of that of the wild-type gene based upon the presence or absence of the labeled nucleotide in the primer.

2. The method of claim 1 wherein the DNA fragment is being screened for a mutation relative to the wild-type gene at the predetermined position and wherein prior to step the sample DNA fragment is separated into at least two aliquots and then in step (b), labeled nucleotide corresponding to the sequence of the wild-type gene at the predetermined position is mixed with one of the aliquots to form a first mixture and labeled nucleotide corresponding to a mutation of the wild-type gene at the predetermined position is mixed with another one of the aliquots to form a second mixture.

3. The method of claim 1 wherein the sample DNA fragment is being screened for a mutation responsible for cystic fibrosis.

4. The method of claim 1 wherein the sample DNA is being screened for a mutation responsible for hemophilia B.

5. The method of claim 1 wherein prior to step (b) the sample DNA fragment is separated into at least two aliquots and then in step (b), labeled nucleotide corresponding to the sequence of a first variant of the wild-type gene at the predetermined position is mixed with one of the aliquots to form a first mixture and labeled nucleotide corresponding to a second variant of the wild-type gene at the predetermined position is mixed with another one of the aliquots to form a second mixture.

6. A method for screening an organism for genetic diseases or gene sequence variation resulting from a nucleotide substitution, translocation, insertion or deletion at a predetermined position, the sequence in the corresponding wild-type gene and normal variations thereof at that position being known, the method comprising
    (a) providing a sample DNA fragment from the genome of that organism which contains the predetermined position,
    (b) providing the sample DNA fragment as a single stranded molecule,
    (c) mixing the single stranded molecule with an inducing agent, a primer having a nucleotide sequence complementary to a region flanking the predetermined position, and a labeled nucleotide to form a mixture, the mixture having an essential absence of nucleotides constituted of bases other than the base of which the labeled nucleotide is constituted,
    (d) subjecting the mixture to conditions conducive for the formation of double stranded hybrids comprising the primer and the single stranded molecule and the formation of a primer extension product incorporating the labeled nucleotide,
    (e) denaturing the double stranded hybrids formed in the mixture in step (d),
    (f) analyzing the denatured double stranded hybrids for the presence of primer extension product incorporating labeled nucleotide, and
    (g) determining whether the sequence of the DNA fragment at the predetermined position is the same as or a variant of the wild-type gene.

7. The method of claim 6 wherein the sample DNA fragment is being screened for a mutation relative to the wild-type gene at the predetermined position and wherein prior to step (c) the sample DNA fragment is separated into at least two aliquots and then in step (c), labeled nucleotide corresponding to the sequence of the wild-type gene at the predetermined position is mixed with one of said at least two aliquots to form a first mixture and labeled nucleotide corresponding to a mutation of the wild-type gene at the predetermined position is mixed with another one of said at least two aliquots to form a second mixture.

8. The method of claim 6 wherein the organism is being screened for cystic fibrosis.

9. The method of claim 6 wherein the organism is being screened for hemophilia B.

10. The method of claim 6 wherein prior to step (c) the sample DNA fragment is separated into at least two aliquots and then in step (c), labeled nucleotide corresponding to the sequence of a first variant of the wild-type gene at the predetermined position is mixed with one of said at least two aliquots to form a first mixture and labeled nucleotide corresponding to a second variant of the wild-type gene at the predetermined position is mixed with another one of said at least two aliquots to form a second mixture.

11. A method for comparing the nucleotide sequence of a DNA fragment of a gene at a predetermined position relative to the nucleotide sequence of the corresponding wild-type gene, the sequence of the wild-type gene being known, the method consisting essentially of the steps of:

(a) providing the DNA fragment as a single stranded molecule in solution, (b) mixing the single stranded molecule with an inducing agent, a primer having a nucleotide sequence complementary to a region flanking the predetermined position, and a labeled nucleotide to form a mixture, the mixture having all essential absence of nucleotides constituted of bases other than the base of which the labeled nucleotide is constituted, (c) subjecting the mixture to conditions conducive for the annealing of the primer to the single stranded molecule and the formation of a primer extension product incorporating the labeled nucleotide, (d) after step (c), subjecting the mixture to gel electrophoresis under denaturing conditions, and (e) determining whether the sequence of the DNA fragment at the predetermined position is the same as or a variant of the wild-type gene.

12. The method of claim 11 wherein the DNA fragment is being screened for a mutation relative to the wild-type gene at the predetermined position and wherein prior to step (b) the sample DNA fragment is separated into at least two aliquots and then in step (b), labeled nucleotide corresponding to the sequence of the wild-type gene at the predetermined position is mixed with one of the aliquots to form a first mixture and labeled nucleotide corresponding to a mutation of the wild-type gene at the predetermined position is mixed with another one of the aliquots to form a second mixture.

13. The method of claim 11 wherein the sample DNA fragment is being screened for a mutation responsible for cystic fibrosis.

14. The method of claim 11 wherein the sample DNA is being screened for a mutation responsible for hemophilia B.

15. The method of claim 11 wherein prior to step (b) the sample DNA fragment is separated into at least two aliquots to and then in step (b), labeled nucleotide corresponding to the sequence of a first variant of the wild-type gene at the predetermined position is mixed with one of the aliquots to form a first mixture and labeled nucleotide corresponding to a second variant of the wild-type gene at the predetermined position is mixed with another one of the aliquots to form a second mixture.

16. A method for screening a DNA fragment of a gene for variation of nucleotide sequence at a predetermined position relative to the nucleotide sequence of the corresponding wild-type gene, the sequence of the wild-type gene being known at the predetermined position, the method comprising:

(a) providing the DNA fragment as a single stranded molecule;

(b) mixing the single stranded molecule with an inducing agent, an unlabeled primer having a nucleotide sequence complementary to a region flanking the predetermined position, and a labeled nucleotide to form a mixture, the mixture having an essential absence of nucleotides that would eliminate the specificity of a primer extension reaction of step (c);

(c) subjecting the mixture to conditions conducive for annealing of the primer to the single stranded molecule and the formation of a primer extension product incorporating the labeled nucleotide at a position complementary to the predetermined position;

(d) after step (c), analyzing the mixture for the presence or absence of primer extension product incorporating the labeled nucleotide, the analysis being carried out under conditions such that any primer which did not form a primer extension product incorporating the labeled nucleotide in step (c) is present throughout the analysis; and (e) determining whether the sequence of the DNA fragment at the predetermined position is the same as or a variant of that of the wild-type gene based upon the presence or absence of the labeled nucleotide in the primer.

17. The method of claim 16 wherein the mixture formed in step (b) has an essential absence of deoxynucleotides constituted of bases other than the base of which the labeled nucleotide is constituted.

18. The method of claim 16 wherein the labeled nucleotide is a deoxynucleotide.

19. The method of claim 16 wherein the labeled nucleotide is a deoxynucleotide and the mixture formed in step (b) has an essential absence of deoxynucleotides constituted of bases other than the base of which the labeled deoxynucleotide is constituted.

20. The method of claim 16 wherein the primer has a nucleotide sequence complementary to a region immediately flanking the predetermined position.

* * * * *

UNITED STATES PATENT AND TRADEMARK OFFICE
CERTIFICATE OF CORRECTION

PATENT NO.    : 5,846,710
DATED         : December 8, 1998
INVENTOR(S)   : S. Paul Bajaj It is certified that error appears in the above-identified patent and that said Letters Patent is hereby corrected as shown below:

Column 1,
Line 8, insert the following:

-- STATEMENT OF FEDERALLY SPONSORED RESEARCH OR DEVELOPMENT

The U.S. Governement has a paid-up license in this invention and the right in limited circumstances to require the patent owner to license others on reasonable terms as provided for by the terms of Grant No. HL36365 awarded by the National Institutes of Health.--

Signed and Sealed this

Sixteenth Day of July, 2002

*Attest:*

*Attesting Officer*

JAMES E. ROGAN
*Director of the United States Patent and Trademark Office*